United States Patent [19]
Altendorf

[11] Patent Number: 6,067,157
[45] Date of Patent: May 23, 2000

[54] DUAL LARGE ANGLE LIGHT SCATTERING DETECTION

[75] Inventor: Eric H. Altendorf, Edmonds, Wash.

[73] Assignee: University of Washington, Seattle, Wash.

[21] Appl. No.: 09/169,533

[22] Filed: Oct. 9, 1998

[51] Int. Cl.$^7$ .................................................. G01N 21/00
[52] U.S. Cl. ........................ 356/337; 356/338; 356/343
[58] Field of Search .................... 356/337–343, 356/349, 38, 73, 442, 318, 72, 317; 250/573–575, 461.2

[56] References Cited

U.S. PATENT DOCUMENTS

| | | | |
|---|---|---|---|
| 4,490,042 | 12/1984 | Wyatt | 356/340 |
| 4,662,742 | 5/1987 | Chupp | 356/39 |
| 5,017,497 | 5/1991 | de Grooth et al. | 436/63 |
| 5,280,272 | 1/1994 | Nagashima et al. | 340/630 |
| 5,510,267 | 4/1996 | Marshall | 436/63 |
| 5,760,900 | 6/1998 | Ito et al. | 356/338 |

OTHER PUBLICATIONS

U.S. application No. 08/823,747, filed Mar. 26,1997.
U.S. application No. 09/080,619, filed May 18, 1998.
Altendorf, E. et al., "Differential blood cell counts obtained using a microchannel based flow cytometer," *Transducers'97*, Int. Conf. On Solid–State Sensors and Actuators, Chicago, Jun. 18–19, 1997, pp. 531–534.

Miyake, R. et al., "A development of micro sheath flow chamber," Proceedings of the IEEE micro electro mechanical systems workshop, Nara, Japan [1991] 265–270.

Salzman, G.C. et al. (1975), "Cell Classification by Laser Light Scattering: Identification and Separation of Unstained Leukocytes," Acta Cytologica 19:374–377 [1975].

Sobek, D. et al., "Microfabricated fused silica flow chambers for flow cytometry," Solid–State Sensor and Actuator Workshop, Hilton Head Island, South Carolina [1994].

Terstappen, L.W.M.M. et al. (1988), "Four–Parameter White Blood Cell Differential Counting Based on Light Scattering Measurements," Cytometry 9:39–43 [1988].

*Primary Examiner*—Frank G. Font
*Assistant Examiner*—Michael P. Stafira
*Attorney, Agent, or Firm*—Greenlee, Winner and Sullivan, P.C.

[57] ABSTRACT

An optical analyzer with a configuration particularly suitable for use with planar liquid sample flow cells is provided comprising a polarized light source and at least two large angle scattered light photodetectors positioned respectively at acute, and right or oblique angles to the incident light beams. Differences in intensities of light measured at the two photodetectors are used to quantify components of the sample.

31 Claims, 10 Drawing Sheets

—— s-polarized

······ p-polarized

——— s-polarized
· · · · · · p-polarized

DUAL LARGE ANGLE LIGHT SCATTERING DETECTION

FIELD OF THE INVENTION

This invention relates to an apparatus and method for the classification of white blood cells using two large angle light scattering channels.

BACKGROUND OF THE INVENTION

Optical flow cytometry is an established means of counting and classifying particles contained within a fluidic sample (Shapiro, H. M., *Practical flow cytometry*, Third Edition, Wiley-Liss publishers, New York, 1995). One application involves the analysis of a blood sample for the purposes of determining the numbers of platelets, red blood cells (RBCs), and white blood cells (WBCs) per unit volume. This is a common clinical measurement, and optical cytometers have been incorporated into a number of commercial hematology analyzers. Recently, microfluidic techniques have been employed for the purposes of developing cytometers which require smaller sample and reagent volumes (Altendorf, E. et al., "Differential blood cell counts obtained using a microchannel based flow cytometer," *Sensors and Actuators* [1997] 1:531–534; Sobek, D. et al., "Microfabricated fused silica flow chambers for flow cytometry," Solid-State Sensor and Actuator Workshop, Hilton Head Island, S.C. [1994]; Miyake, R. et al., "A development of micro sheath flow chamber," Proceedings of the IEEE micro electro mechanical systems workshop, Nara, Japan [1991] 265–270). Analytical instruments based on these efforts will be smaller and more portable than conventional devices.

Knowledge of the number and nature of blood cells is important for disease diagnosis. For this reason, complete blood counts and white cell differentials are common clinical diagnostic tests carried out using a hematology analyzer. Forward angle light scattering (FALS) is sensitive to particle size and can be used to distinguish platelets from red blood cells. Small angle scattering (SALS) or large angle light scattering (LALS) in combination with FALS can distinguish within the WBCs between granulocytes, lymphocytes and monocytes (Salzman, G. C. et al. (1975), "Cell Classification by Laser Light Scattering: Identification and Separation of Unstained Leukocytes," Acta Cytologica 19:374–377). However, within the granulocytes, SALS and FALS cannot clearly distinguish between eosinophils and the remaining granulocytes such as neutrophils and basophils.

The difference in intensity of scattered light between s-polarized and p-polarized light can be used to further distinguish between the granulocytes. At small angles scattering of the two polarizations is indistinguishable. At large angles, WBC sized structures with no internal structure show only a small difference between the scattered light intensity of the two polarizations. Granulocyte WBCs, having an internal structure comprising numerous small granules, exhibit a difference in scattering intensity between the polarizations. In eosinophils the granules are birefringent and act to depolarize the scattered light, thereby reducing the difference in scattering intensity between the two polarizations. This depolarization has been used to distinguish cell types (Terstappen, L.W.M.M. et al. (1988), "Four-Parameter White Blood Cell Differential Counting Based on Light Scattering Measurements," Cytometry 9:39–43; de Grooth et al., U.S. Pat. No. 5,017,497; Marshall, U.S. Pat. No. 5,510,267. The depolarization was measured by impinging polarized light on a sample, collecting the large angle scattered light at a single large angle, splitting the collected light into two beams and measuring the scattered light in the two beams using two detectors, one for orthogonal light scattering of all polarizations, and the second preceded by a polarizing filter to measure depolarized orthogonal light scattering.

SUMMARY OF THE INVENTION

This invention provides an analyzer and a method for distinguishing polarization-preserving particles from depolarizing particles without requiring polarizing filters. This analyzer is especially useful with planar flow cells but can also be used with conventional round flow cytometers. The analyzer comprises a polarized light source positioned to produce a light beam which intersects a liquid sample flow in a flow cell. Light scattered by particles in the sample is measured by a first and a second large angle light scattering channel, positioned to receive scattered light at large angles $\theta_1$ and $\theta_2$, respectively. Each LALS channel comprises a photodetector and collection optics. No polarizing or wavelength filters are required as part of the LALS detection channels. The scattered intensity at each channel is obtained and the relative intensities are used to classify the particles. While this invention can be used with any type of flowing particle, it is particularly suited to a hematology analyzer used to count and classify blood cells, and in particular eosinophils. Preferably $\theta_1$, is between about 15° and about 50°, more preferably about 30°±10°, and most preferably about 39°±10° where the flow cell is positioned at an oblique angle to the light beam. Preferably, $\theta_2$ is between about 50° and about 130°, more preferably about 90°±15°, or about 115°±10°, and most preferably about 73°±10° where the flow cell is positioned at an oblique angle to the light beam.

The flow cell is preferably planar and positioned at Brewster's angle to the light beam, which for glass and plastic windows in the flow cell is about 56°. The analyzer can further include small angle and forward angle light scattering channels, which can be used to distinguish between particles based on size and shape. The forward angle light scattering (FALS) detector is preferably placed at an angle $\theta_F$ of between about 0.5 and about 3°, although it can be placed at a 0° angle for absorption measurements. When the FALS detector is used for absorbance measurements with a laser light source, filters will be required as is known to the art because of the intensity of the light beam. The small angle light scattering detector (SALS) is preferably placed at an angle $\theta_S$ greater than $\theta_F$, of between about 2° and about 10°. The analyzer can further include an absorption channel for measuring particles containing absorptive species such as dyes, hemoglobin and bilirubin. The absorption measurement can be carried out in the same stream as the scattering measurement, in the same or a different measurement zone, or in a separate stream. The absorption channel comprises a light source positioned to illuminate a sample flow, collection optics positioned to collect the transmitted light, and a photodetector. The collection optics can include a wavelength filter. The analyzer can further include additional detectors such as a second absorption channel comprising collection optics with a second wavelength filter and a photodetector. The analyzer can further include a fluorescence channel, comprising a fluorescence photodetector and fluorescence collection optics. The fluorescence channel can utilize the scattering light source or a separate light source.

This invention also provides a method for distinguishing polarization preserving particles from depolarizing particles, comprising the steps of: flowing said particles through a p-polarized light beam; measuring the scattered light intensity $I(\theta_1)$ at a first large angle, $\theta_1$; measuring the scattered light intensity $I(\theta_2)$ at a second large angle, $\theta_2$, wherein $\theta_2 > \theta_1$; and comparing $I(\theta_1)$ to $I(\theta_2)$, thereby distinguishing polarization preserving particles from depolarizing particles.

DETAILED DESCRIPTION OF THE INVENTION

Figure 1:
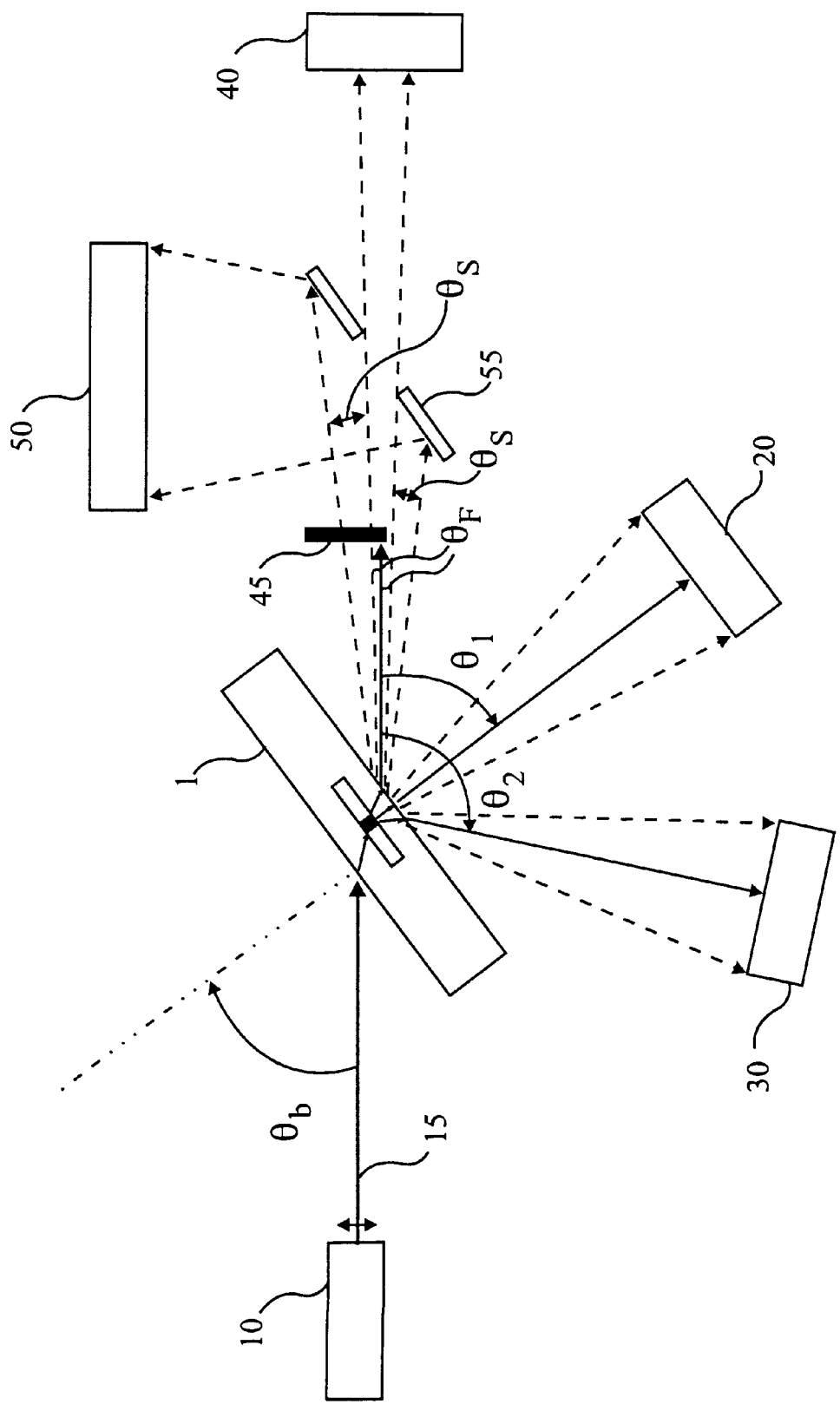
FIG. 1 is an analyzer employing dual LALS detection.

The analyzer with dual LALS detection with the laser beam oriented at Brewster's angle to the planar flow cell is illustrated in FIG. 1. The analyzer is used with a sample flow, in this embodiment confined in flow cell 1. The analyzer comprises polarized light source 10 for directing polarized light beam 15, in this embodiment p-polarized, at the sample flow. The region where the light beam strikes the flow is the scattering measurement zone. The light source can be a laser, preferably a He—Ne laser, or it can be a non-laser light source such as an arc lamp. It can be intrinsically polarized, as is a laser, or it can include an external polarizer. To minimize reflection losses at the flow cell windows, the light beam is oriented at Brewster's angle $\theta_b$ to an imaginal line normal to the flow cell. For glass or plastic windows $\theta_b$ is about 56°.

If a laser beam is incident on a planar flow cell such that the beam is normal to the surface of the cell, then due to internal reflections scattering angles greater than about 50° and less than 140° cannot be accessed. Tilting the flow cell relative to the incident beam allows light scattering at larger angles to be detected. If the beam is further incident at the Brewster angle $\theta_b$ and if the incident laser beam is polarized parallel to the plane containing the reflected and refracted beams (p-polarization), then losses due to reflections at the interfaces can be minimized. This angle minimizes the amount of light reflected from the flow cell window interfaces allowing more of the laser light to interact with the sample stream. In order to make use of this optical property, the light is p-polarized as shown. This is a requirement to minimize light loss and reflection at internal and external interfaces.

Angular orientations given herein are with respect to the propagation direction of beam 15 unless otherwise stated. Note that the beam is refracted by the cell so the propagation direction within the scattering measurement zone is different from the direction before the flow cell. The analyzer further includes first LALS detector 20 and second LALS detector 30. This embodiment also includes SALS detector 50 and SALS mirror 55 which directs the SALS to the detector. It also includes FALS detector 40 and beam block 45 which prevents beam 15 from striking the FALS detector. The photodetectors are preferably photodiodes. Each detector can be coupled with the scattering measurement zone using detection optics. The optics for each detection channel typically include one or more lenses to gather light, and a field stop to block scattered light outside of the desired collection angles. One aspect of the present invention is that by the use of two LALS detectors it is not necessary to include polarizing or wavelength filters in the collection optics. The angles at which the LALS detectors are positioned are preferably about 28° to about 50° for the first LALS detector 20 and between about 65° and about 81° for the second LALS detector 30.

The dual LALS analyzer can be used to distinguish between agranular particles, granular particles with one or more polarization-preserving granules and granular particles with one or more depolarizing granules. The term particle is used herein for any non-dissolved species in a liquid sample capable of reflecting light, including cells, cell fragments, fluorescent beads, bacteria and other biological particles, polymers, dust, microcrystals and others. The analyzer is particularly suited to leukocyte discrimination, wherein agranular leukocytes include lymphocytes and monocytes, polarization-preserving granular leukocytes include neutrophils and basophils, and depolarizing granular leukocytes include eosinophils. WBC light scattering was modeled as follows.

Figure 2:
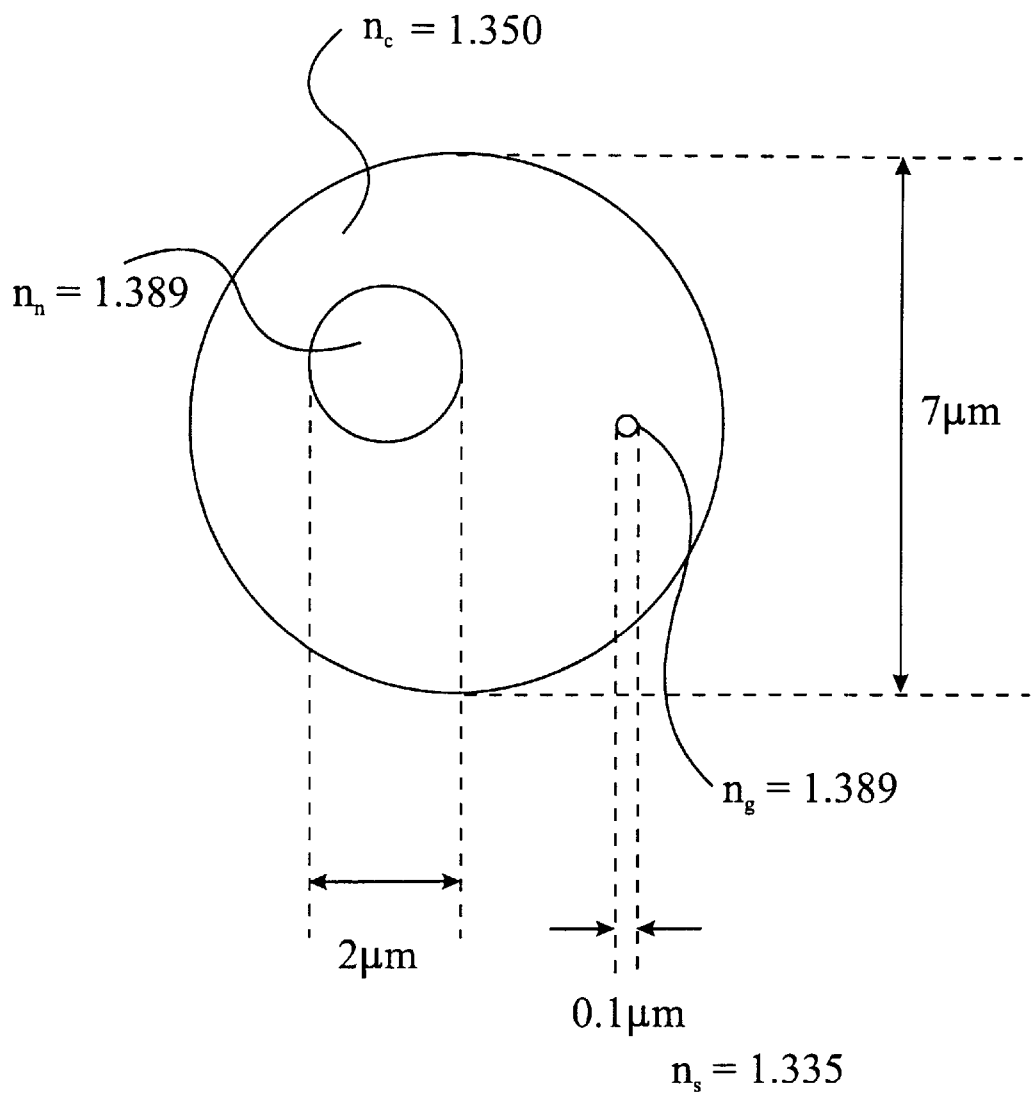
FIG. 2 is a white blood cell model used for Mie scattering calculations.

The blood cell was modeled as a system comprised of three parts, the outer cell membrane and contained cytoplasm, herein called the cell component, a nuclear component, and a granular component, as illustrated in FIG. 2. All three components were modeled as homogenous spheres so that a Mie scattering analysis could be used to model the light scattering. Independent particle scattering (i.e., no multi-particle scattering events) was assumed so that only the light scattering properties of three representative spheres needed to be considered. All membrane effects were ignored, so that the majority of the scattering arises from the bulk of the scattering particle.

The intercellular medium is physiological saline (0.85%) with an index of refraction given by $n_s=1.335$, while the intracellular medium consists of cytoplasm with an index of $n_c=1.35$, as well as nuclear and granular material. The indices for saline and plasma were obtained from *Practical Flow Cytometry*, by H. M. Shapiro, 3rd edition, p. 149. The nuclear and granular material consist of proteins, and the index of refraction of these materials is modeled after the RBC protein hemoglobin. The RBC index of refraction is n=1.389 (Thesis by P. Wing-Poon Cheung, *Effects of Blood Physiological Variations on Optical Scattering and Fiber*

*Optic Oximetry*, University of Washington, 1973) at a wavelength of 660 nm. The nuclear and granular refractive indices are therefore $n_n$, $n_g$=1.389. FIG. 2 illustrates the model as well as the particle dimensions used. The wavelength of the incident light is taken to be $\lambda$=685 nm.

In the model, birefringence-induced scattering was assumed to occur only for eosinophils, and to cause depolarization of the incident p-polarized light into equal components of s- and p-polarized light. Mie scattering calculations were then used to determine the angular distributions of the scattering of these components. The degree of birefringence assumed here for the WBCs is not meant to be exact, and was chosen to demonstrate the underlying principle of the dual LALS approach.

Figure 3:
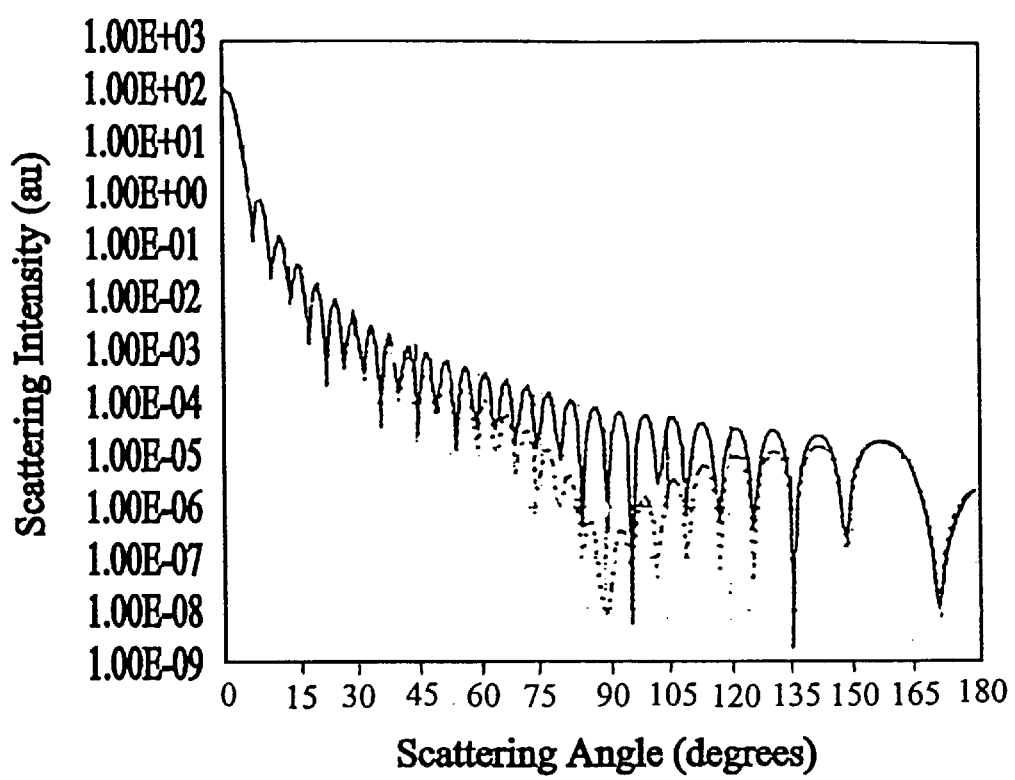
FIG. 3 is the calculated scattering intensity as a function of scattering angle for the outer cell membrane and cytoplasm of the modeled white blood cell.
Figure 4:
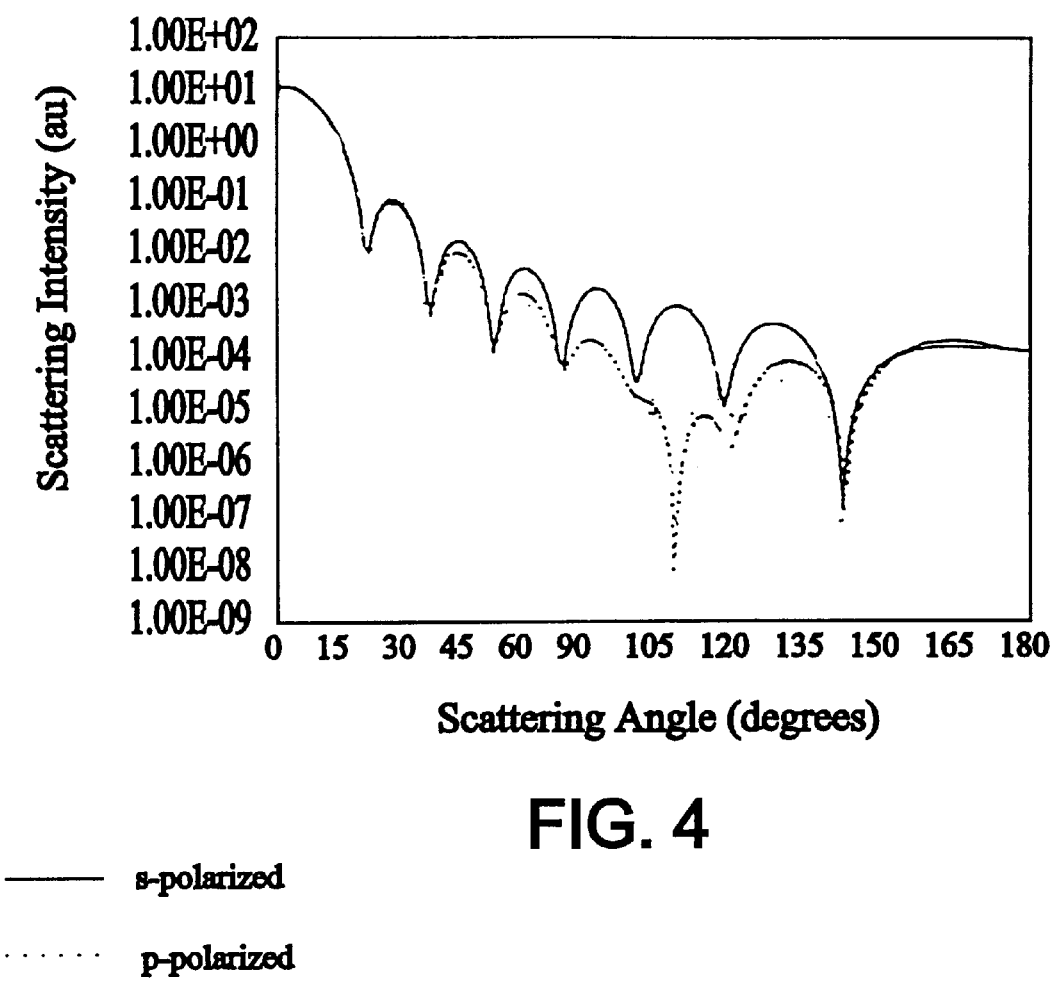
FIG. 4 is the calculated scattering intensity as a function of scattering angle for the nucleus of the modeled white blood cell.
Figure 5:
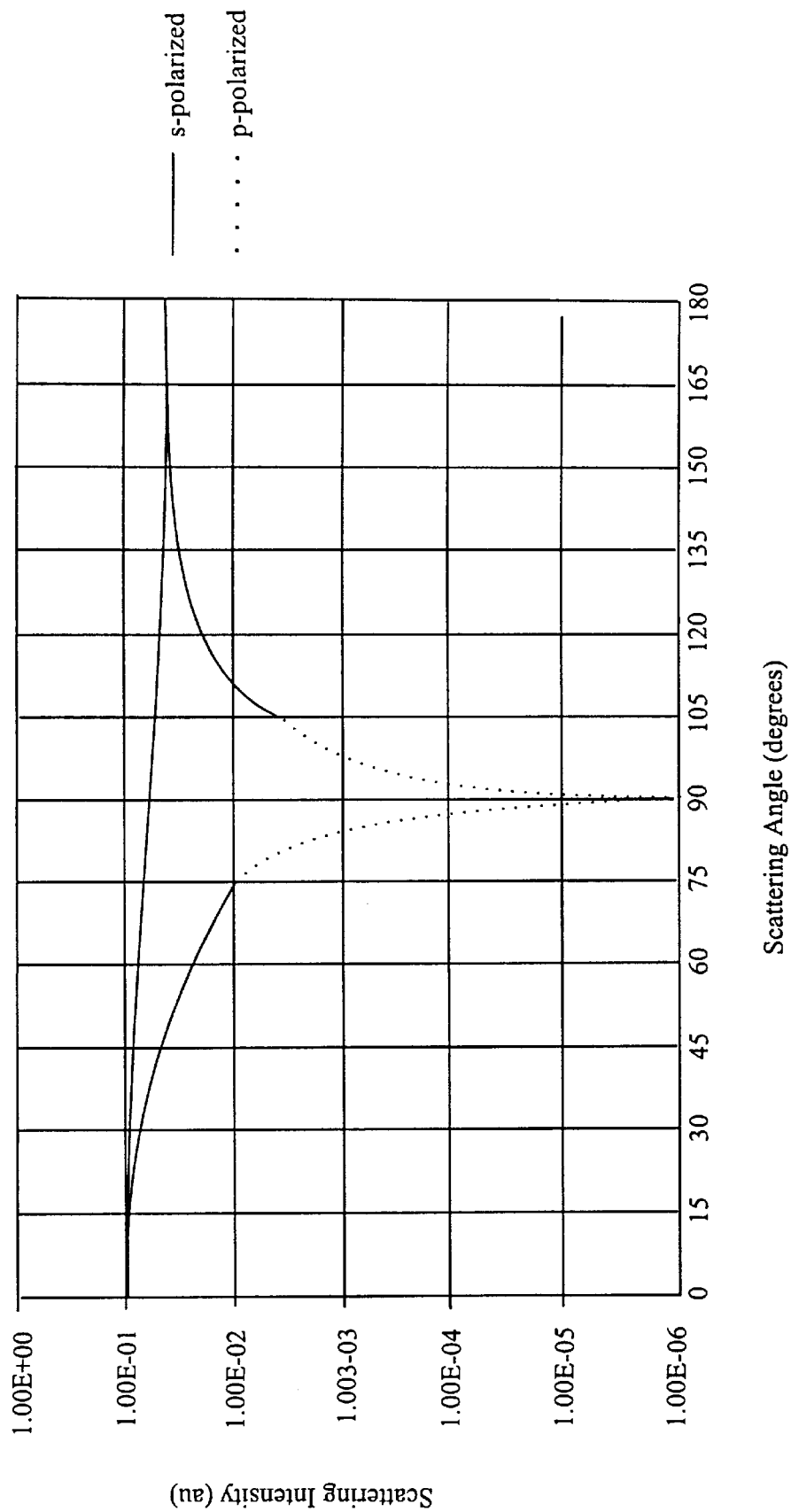
FIG. 5 is the calculated scattering intensity as a function of scattering angle for granules in the modeled white blood cell.

Results from the dual LALS model are shown in FIGS. 3, 4, and 5, which display the calculated Mie scattering for each of the three cellular components. These figures indicate that most of the large angle scattering, and sensitivity to polarization at large angles, is due to the granules. Therefore, for the purposes of this model, only the granule properties were used to represent WBC scattering at large angles. Table 1 displays the LALS intensities at both large angles characteristic of a constructed optical configuration, for s-polarized, p-polarized, and depolarized (equal, s-polarized, and p-polarized) light. Eosinophils, with their birefringent granules, are assumed to behave as if the light were depolarized light. This assumes that the birefringence and scattering mechanisms can be decoupled, i.e., that the birefringence generates new incident light which is then scattered. Non-granulocytes (i.e., lymphocytes and monocytes) have smaller scattering intensities than those in Table 1 due to the absence of granules in these cells.

TABLE 1

MIE scattering results for granules

| LALS detection channel | p-polarized scattering intensity | s-polarized scattering intensity | depolarized scattering intensity |
| --- | --- | --- | --- |
| $\theta_1$ = 39° | 0.112 | 0.184 | 0.148 |
| $\theta_2$ = 73° | 0.0118 | 0.135 | 0.073 |

Figure 6:
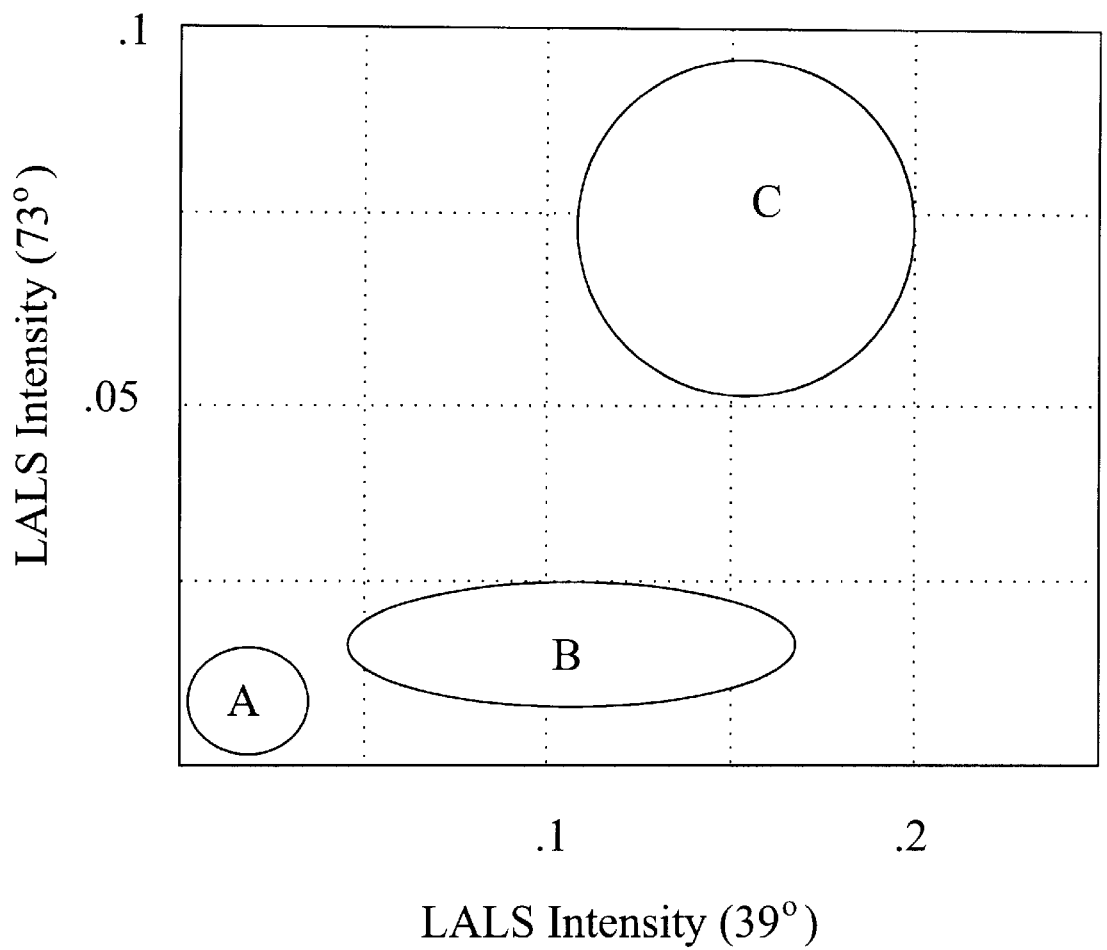
FIG. 6 is the calculated scatter plot for (A) agranular leukocytes (B) granular leukocytes with polarization-preserving granules and (C) granular leukocytes with depolarizing birefringent granules

A calculated scatter plot suggested by Table 1 is shown in FIG. 6, demonstrating how the eosinophils can be distinguished from the remaining white blood cells. The scatter in the plot is caused by the inhomogeneity in the number and size of granules in the cells. The shapes of the scatter plots are merely indications of possible shapes. In the method of distinguishing particles of this invention, the two LALS intensities are compared and the particles are assigned to types on the basis of calculated or measured data as in FIG. 6. As suggested by the figure, the ratio of the two intensities is a characteristic which can be used in assigning particles.

The calculation results shown in FIGS. 3–5 can be used to select angles for the LALS detectors. As shown in FIG. 5, the scattering from granules becomes polarization-sensitive above about 15°, and the maximum difference occurs at 90°. Comparing FIG. 5 to FIGS. 3 and 4 shows that above about 15° granular scattering is predominant over cell and nuclear scattering. To identify granules a scattering angle above about 15° is chosen. To further distinguish depolarizing granules scattering is also measured at a second angle at which there is a marked difference in the scattering of s-polarized and p-polarized light. In a constructed embodiment, LALS detectors were positioned at $\theta_1$=39° and $\theta_2$=73°.

The term large angle light scattering is used herein for scattering at angles at which granule scattering dominates, generally greater than about 15°. In this analyzer the two LALS detectors are at different large angles. As suggested by FIG. 5, the first is positioned between about 15° and 50°, and the second is positioned between about 50° and 130°. For optimum distinction of depolarizing particles, the detectors are at about 30°±10° and 90°±15°. Preferably the LALS detectors are positioned at oblique angles to the light beam. A second consideration in detector placement is the ease of construction. In the embodiment of FIG. 1 having an angled flow cell, the LALS detectors can most conveniently accommodate light scattering at angles of $\theta_1$=39°±10° and $\theta_2$=73°±10°.

In addition to the dual LALS detectors, the analyzer can include a SALS detector and a FALS detector. The term FALS as used herein refers to light scattered at angles which can be used primarily to count particles. The lower limit on the FALS angle is determined by the incident beam shape and size. The FALS detector is preceded by a beam stop, such as an obscuration bar, to prevent the incident beam from directly striking the detector. The FALS angle is an angle allowing measurement of absorption and particle size and is preferably between about 0° and about 3°, more preferably between about 0.50 and about 3°. The term SALS is used herein for angles which, in combination with the FALS signal, can be used primarily to distinguish granular from agranular particles. The SALS angle is an angle providing information about internal structure of particles as shown by their light scattering properties, is greater than the FALS angle, and is preferably between about 2° and about 10°.

The dual LALS analyzer can also include fluorescence measuring for use when the sample has been labeled with a fluorescent dye or if it includes fluorescent beads or other fluorescent particles. For fluorescence excitation the analyzer can utilize the light scattering light source or can alternatively include a separate light source. Preferred light sources for fluorescence excitation are lasers, in particular argon ion lasers. The fluorescence excitation can take place in the scattering measurement zone or at a different region of the sample flow. The fluorescence measurement can use the same sample flow as the scattering measurements or a separate flow. The fluorescence is detected at a large angle to avoid scattered light, preferably greater than about 30°. A wavelength filter in front of the detector can be used to further separate fluorescent from scattered light. The fluorescence photodetector can share collection optics with one of the LALS detectors and, following a collection lens, the light can be separated with a wavelength sensitive beam splitter.

The analyzer can also include absorbance measuring for use with absorbing particles such as cells labeled with a stain, or having hemoglobin or bilirubin. As with the fluorescence measurements, the absorbance measurement can use the same or a different light source than the scattering measurement, positioned on the same or different flow region. Preferred light sources include LEDs. The absorbance is measured with a detector positioned on the opposite side of the sample flow from the light source. As a practical construction consideration, the absorption measurement is preferably performed on a separate flow region with a separate detection channel and light source from the scattering so that both FALS and SALS detectors can be accommodated as well as the absorption detector. The detector can be preceded by a wavelength filter to select the absorption band. More than one detector, each having different wavelength filters can be employed.

Figure 7:
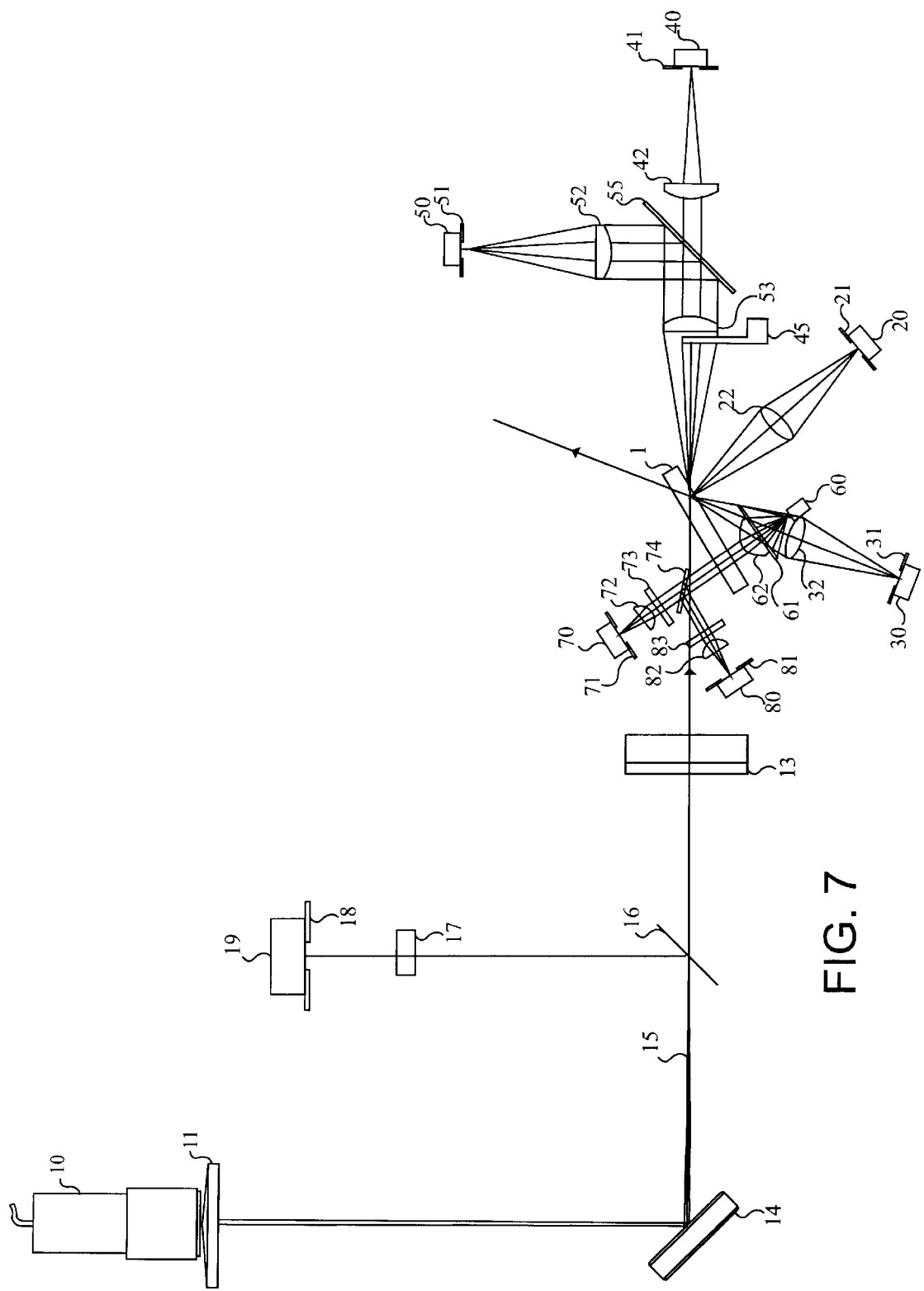
FIG. 7 is an analyzer having dual LALS, SALS, FALS and absorption detection.

FIG. 7 shows a schematic of an embodiment of the analyzer having two large angle light scattering detectors, a forward angle light scattering detector, a small angle light scattering detector, and an absorption measurement means. Laser 10 is used for the light source for the scattering measurements. The light beam 15 is focused using first focusing lens 11 and second focusing lens 13, and is directed to the sample flow in cell 1 by mirror 14. The light beam is partially reflected by a member comprising a material which is both reflective and transparent, such as cover slip 16 and photodiode 19, for monitoring of the laser power. Photodiode 19 is preceded by photodiode lens 17 and photodiode field stop 18. The laser beam intercepts the sample flow in cell 1 to define a light scattering measurement zone. The scattered light is collected at two large angles. At a first large angle the light is collected by first LALS lens 22 and detected by first LALS detector 20, which is preceded by first LALS field stop 21. At a second large angle the light is collected by second LALS lens 32 and detected by second LALS detector 30, which is preceded by second LALS field stop 31. Small angle scattering is collected by SALS/FALS lens 53 in combination with SALS lens 52 and detected by SALS detector 50, which is preceded by SALS field stop 51. It is directed to the SALS detector 50 by mirror 55. Forward angle scattering is collected by SALS/FALS lens 53 in combination with FALS lens 42 and detected by FALS detector 40, which is preceded by FALS field stop 41. Mirror 55 has a hole in the center to permit transmission of the forward angle scattered light. Beam block (obscuration bar) 45 prevents the laser beam from striking FALS detector 40 directly. Sample absorption is measured in a different portion of the sample flow from the light scattering measurement zone. Light from LED 60, focused by LED lens 62 in combination with LED field stop 61, intercepts flow cell 1 to define an absorption measurement zone. Beam-splitting mirror 74 transmits some of the light to first absorbance detector 70 and reflects the remainder to second absorbance detector 80. First absorbance detector 70 is used in combination with filter 73, which selects a first wavelength of light, and absorbance lens 72 and absorbance field stop 71. Second absorbance detector 80 is used in combination with filter 83, which selects a second wavelength of light, LED lens 82 and LED field stop 81.

FIG. 13 shows a further embodiment of this invention which has been developed for cytometry and hematology applications. In this embodiment cylindrical lenses and prisms are used to shape and focus the incident beam into an elliptical profile. This beam is directed through the flow cell at Brewster's angle $\theta_b$ by means of two mirrors. Laser 10 directs light beam 15 through a first pair of anamorphic prisms 88 through first focusing lens 11 and a second pair of anamorphic prisms 84. The prisms broaden the beam in one direction and narrow it in another to form the elliptical profile. The elliptical beam strikes mirror 14, which directs light beam 15 through second focusing lens 13 to second mirror 86 which directs it to flow cell 1. FALS detector 40 preceded by FALS lens 42 measures light reaching it through a hole in SALS mirror 55 preceded by SALS/FALS lens 53. Light reflected from SALS mirror 55 is measured by SALS detector 50 preceded by SALS lens 52. First LALS detector 20 preceded by first SALS lens 22 measures large angle scattered light. The second large angle detector 30 and second LALS lens 32 which precedes it have been moved from their positions shown in FIG. 7 to the other side of flow cell 1 to avoid background stray light reflected by the FALS field stop. The FALS and SALS detectors are photodiodes and the LALS detectors are miniature photomultiplier tubes.

The actual scattering angles collected by this system are: FALS detector—1.43–2.15°; SALS detector—2.15–8.44°; first LALS detector—28.2–49.2°; second LALS detector—107–127°.

EXAMPLE

Microfluidic laminate-based structures incorporating hydrodynamic focusing and flow channels with dimensions much less than 1 mm were fabricated and used to transport and analyze blood samples. Optically transparent windows integral to the flow channels were used to intercept the sample streams with a tightly focused diode laser probe beam. The size and structure of the blood cells passing through the laser beam determined the intensity and directional distribution of the scattered light generated. Forward and small angle light scattering channels were used to count and differentiate platelets, red blood cells, and various populations of white blood cells. All the blood samples used were characterized using a commercial hematology analyzer for comparison and validation purposes.

In order to count and classify blood cells in the manner described above, the cells must be made to pass one at a time through the incident laser beam. Traditionally this is done by using hydrodynamic focusing where the blood cell sample stream is encircled and combined in appropriate proportions with a sheath fluid stream, and both fluids are made to pass through a tapered orifice or flow channel. The hydrodynamic forces of the flowing and constricting sheath fluid then cause the sample stream to form a narrow thread of flowing cells.

Microfluidic structures can be used to spatially confine blood cells in very narrow and precisely formed channels without the need for a sheath fluid. Such microstructures cannot, however, typically accommodate high flow rates due to the shear stresses generated. The microcytometer used in this invention confines both the sample and sheath streams within a microchannel of appropriate dimensions for the assays intended.

All the experiments were performed in laminate-based planar microstructures manufactured by Micronics, Inc., Redmond Wash., as described in U.S. patent applications Ser. No. 08/823,747 filed Mar. 26, 1997, and 09/080,691 filed May 18, 1998, incorporated herein by reference to the extent not inconsistent herewith. One such device was comprised of two thin glass windows separated by a 100$\mu$ thick adhesive layer into which flow channels were cut. This device produced a focusing of the sample stream in one plane only, and hence is referred to herein as the 2-D flow cell. The cross-sectional dimensions of the channel containing the focused cell stream was 100$\mu$ by 1 mm. A second structure was formed from Mylar and Mylar-laminate sheets (3M, Austin, Tex.). The channels were cut with a $CO_2$ laser system (ULS-25E, Universal Laser Systems, Scottsdale Ariz.). This device produced a focusing of the sample stream by fully encircling the sample stream with a sheath fluid stream, and is referred to herein as the 3-D flow cell. The cross-sectional dimensions of the channel containing the focused cell stream in this device were 100$\mu$ by 500$\mu$. A custom control station consisting of two computer-controlled syringe pumps (Kloehn Company, Ltd. , Las Vegas Nev.) was used to provide constant sheath and sample flow rates in the micro-structures. The sample flow rate was 95 nl/s in the 2-D flow cells and 400 nl/s in the 3-D flow cells. A 9 mw, 685 nm wavelength diode laser module (Melles Griot, Boulder Colo.), which produced a near circular collimated 4 mm diameter beam, was used as the light source. The laser beam passed through two crossed cylindrical lenses in order to produce a focused elliptical beam with dimensions perpendicular to the direction of propagation of 13µ by 105µ at the sample stream. Two high speed narrow format scanning photodiode detectors (Centro Vision, Newbury Park Calif.) were used to collect the FALS (1.4° to 2.2°) and SALS (2.2° to 8.4°) signals. An obscuration bar was used to block the direct laser beam from impinging on the detectors, and three lenses and a custom mirror with a central aperture (hole) were used to direct the scattered light to the detectors. Electronics signals were collected with an AT-MIO-16E-1 data acquisition board (National Instruments, Austin Tex.) when using the 2-D flow cell, and with a custom high speed data acquisition system when using the 3-D flow cell.

All blood samples (human) were collected with vacutainer (Becton Dickinson, Franklin Lakes N.J.) tubes containing the anticoagulant EDTA, prior to preprocessing and dilution. For the RBC and platelet assays, dilution of the samples with phosphate buffered saline was carried out by external manual mixing prior to introduction to the flow system. For the white blood cell assays, external mixing of the blood sample with a commercial soft lysing reagent (Streck-Sheath, Streck Laboratories, Omaha Nebr.) was carried out prior to introduction to the instrument. Times between mixing and analysis in both cases were kept to a minimum to avoid excess lysing of white cells or osmotic distortion of the RBCs and platelets. Aliquots of all the original samples, as well as aliquots of the mixed and diluted samples where possible, were analyzed with a commercial hematology analyzer (Cell-Dyn 3500R, Abbott Laboratories, Ill.) for comparison and control purposes.

Figure 8:
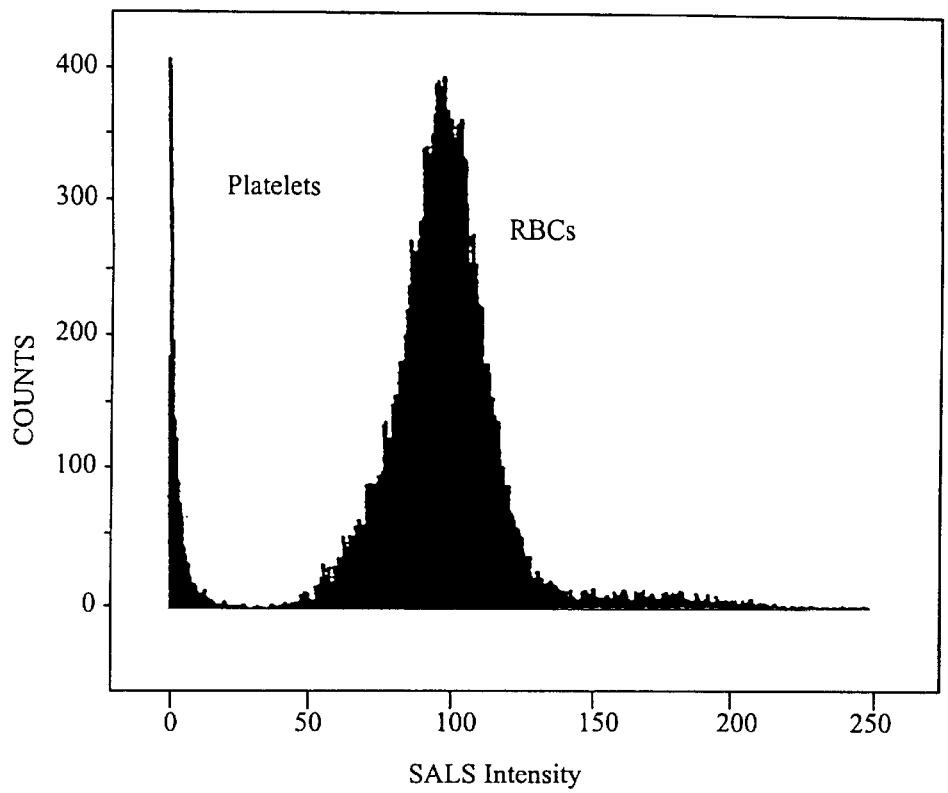
FIG. 8 plots small angle light scattering pulse amplitudes for red blood cells and platelets.
Figure 9:
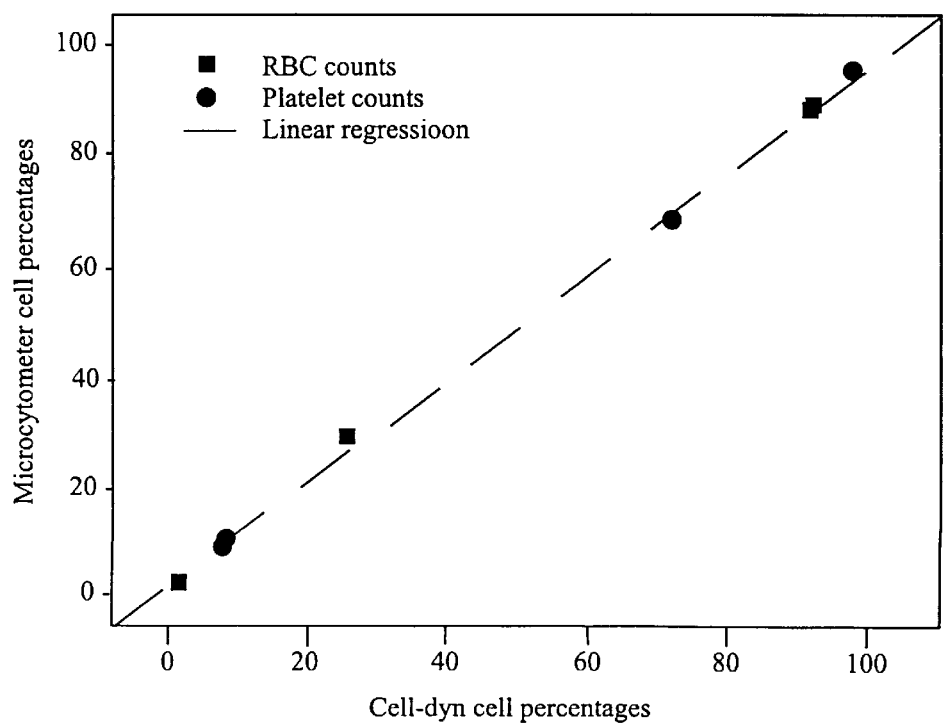
FIG. 9 compares results of red blood cell and platelet measurements determined using the methods of this invention with results using a commercial hematology analyzer.

FIG. 8 displays results obtained using a 1:400 prediluted sample of whole blood and a 2-D flow cell. A histogram of the SALS light scattering pulse amplitudes is shown indicating a biomodal distribution corresponding to platelets and RBCs. Integration of the area under each of the peaks was used to determine the relative percentages of RBCs and platelets in the sample. These results along with data obtained from three additional samples are plotted in FIG. 9 against RBC and platelet percentages obtained using the Cell-Dyn 3500R. FIG. 9 indicates a good correlation between the two methods.

Figure 10:
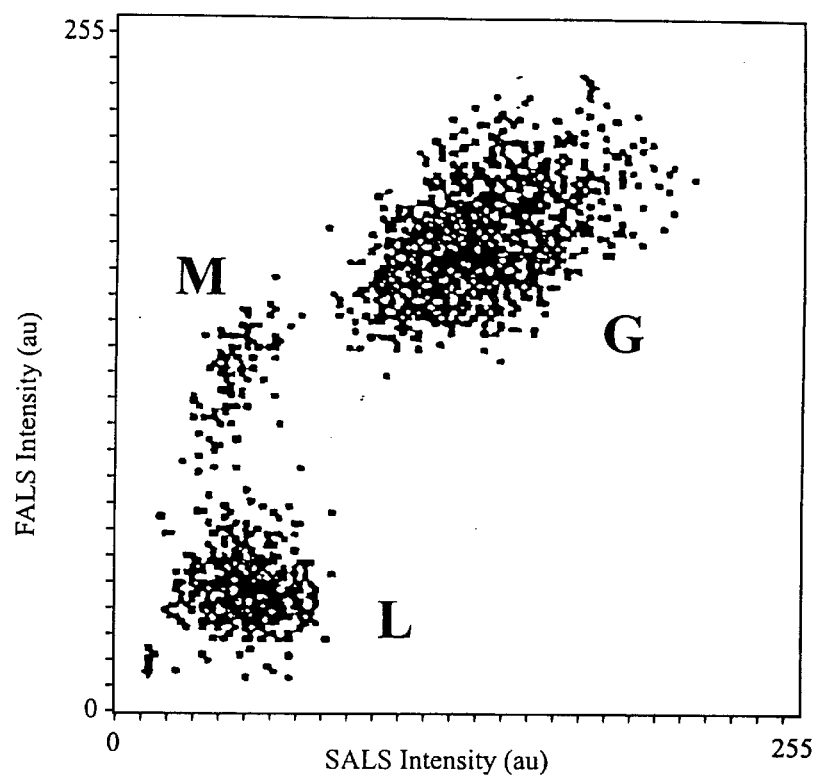
FIG. 10 is a 2-D histogram of the FALS and SALS data from a whole blood sample diluted 1:50 showing lymphocytes (L), monocytes (M) and granulocytes (G).
Figure 11:
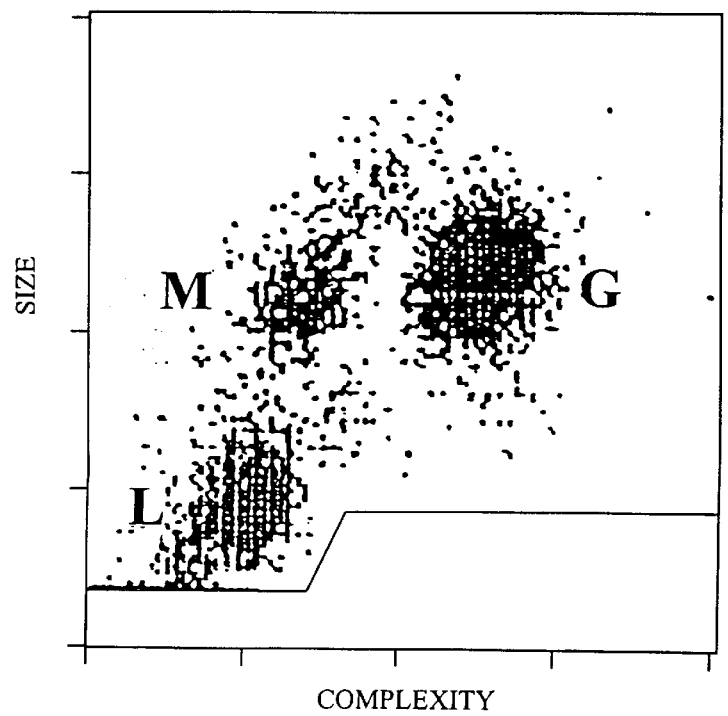
FIG. 11 shows an analysis of the sample of FIG. 10 using a commercial hematology analyzer.

FIG. 10 displays results obtained using a whole blood sample diluted 1:50 in the commercial soft lyse reagent, and a 3-D flow cell in the form of a 2-D histogram of the FALS and SALS data. An analysis of an aliquot of the same sample by the Cell-Dyn 3500R is shown in FIG. 11. The three dominant clusters in each plot correspond to lymphocytes (L), monocytes (M), and granulocytes (G). The microcytometer, and commercial analyzer produce similar degrees of cluster resolution. The relative cell counts (to the total white cell count) obtained with the microcytometer are 27.0% (L), 9.31% (M), and 63.7% (G), which are also in good agreement with the Cell-Dyn percentages of 26.9% (L), 9.68% (M), and 63.4% (G).

Figure 12:
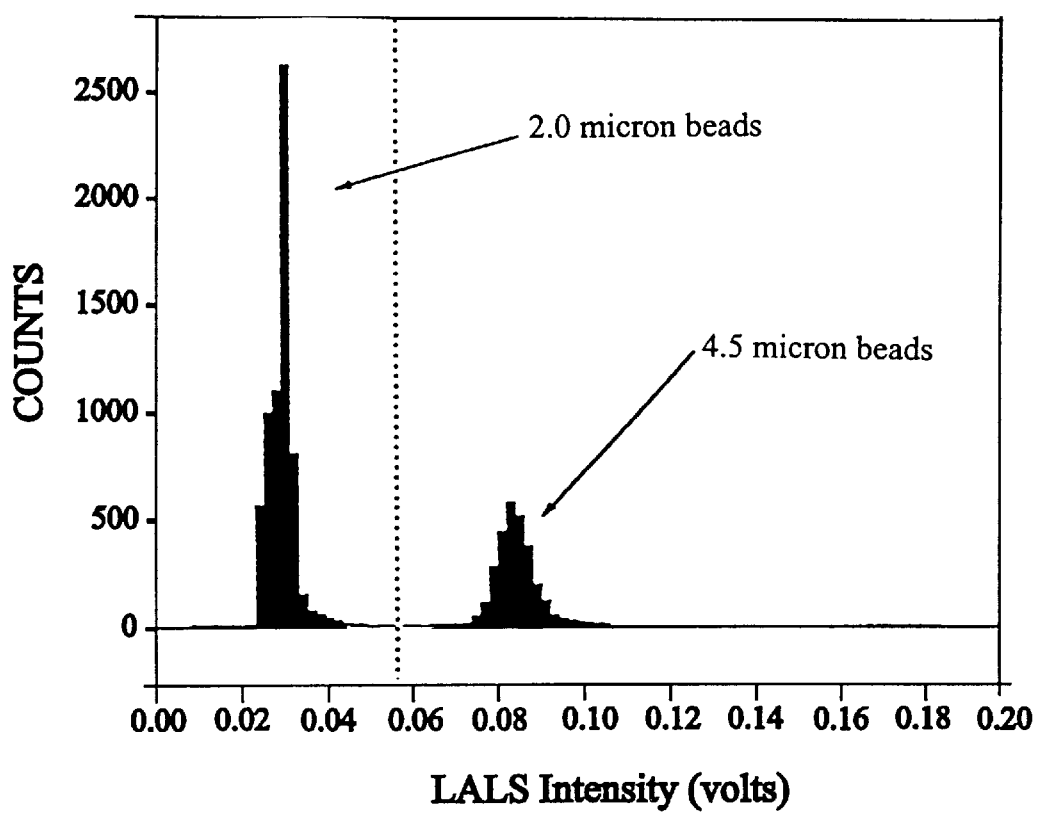
FIG. 12 shows large angle light scattering data for 2.0 and 4.5µ microspheres.
Figure 5:
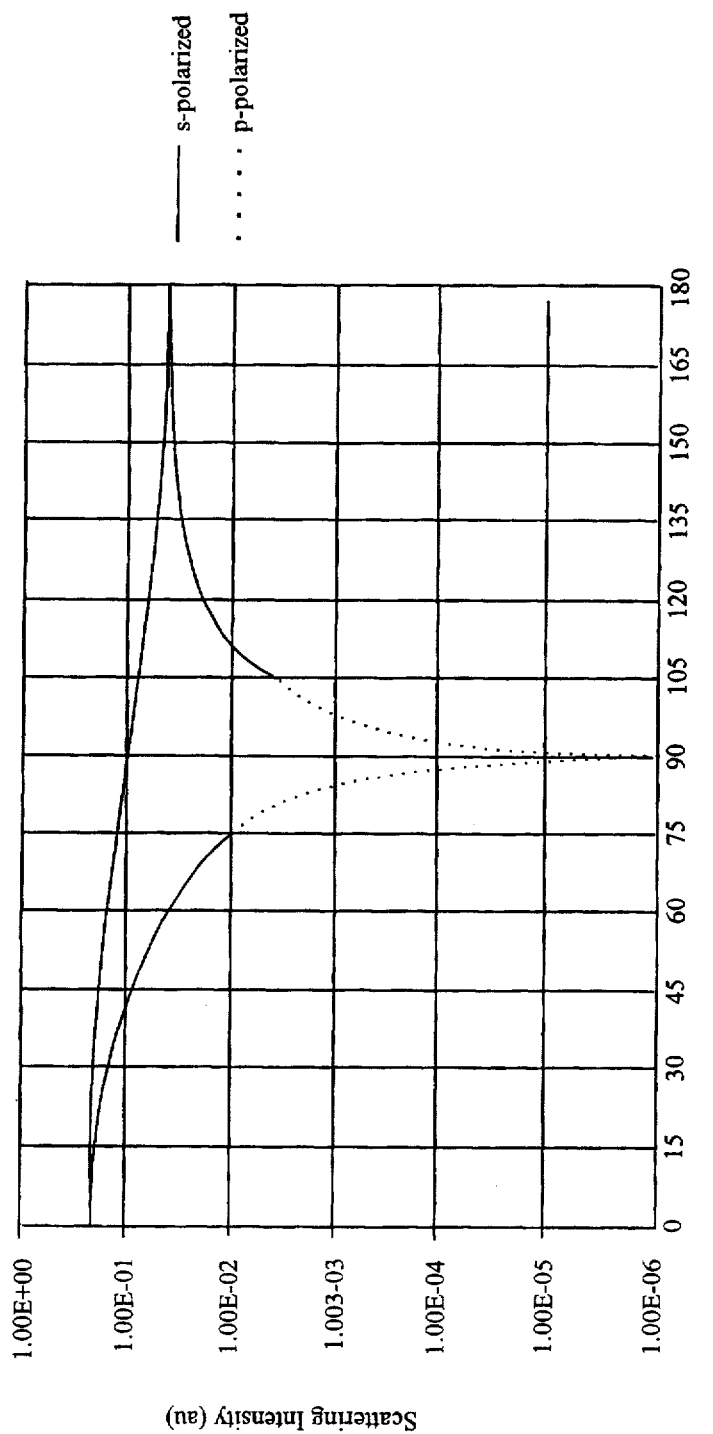
Figure 6:
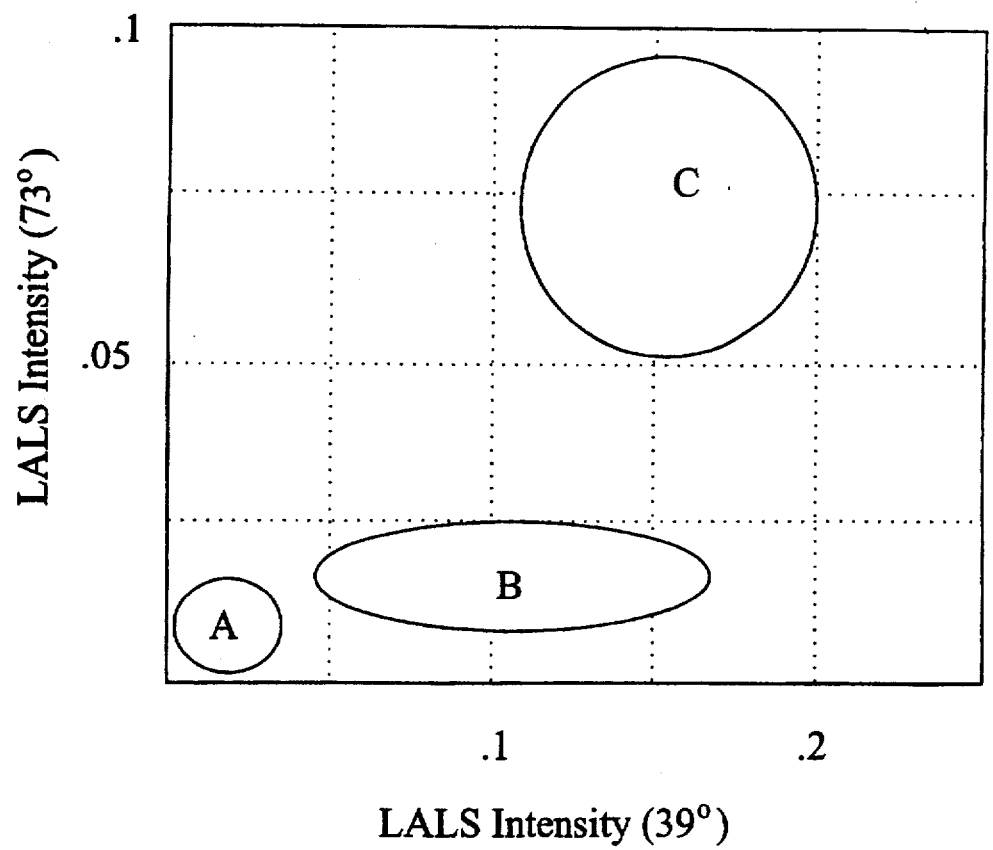

FIG. 12 shows large angle light scattering data for a flow sample containing 2.0 and 4.5µ microspheres used for calibrating and testing instrument performance.

The microcytometer and method described herein has demonstrated the ability of counting and classifying platelets, RBCs, various white cell populations and other particles by means of laminar flow-based microfluidic flow channels and light scattering optics.

This invention has been described and illustrated with respect to specific components; however, as will be appreciated by one skilled in the art, other equivalent components may be substituted for those described herein. For example, the LALS and other detectors may be used to detect absorbance, fluorescence, or other signals as well as scattered light from a laser source, and multiple (more than two) LALS detectors may be used. Additional SALS and FALS detectors may also be used to collect additional information.

We claim:

1. An optical analyzer comprising:
   a p-polarized light source positioned to produce a light beam which intersects a sample flow, said intersection defining a scattering measurement zone;
   a first angle light scattering photodetector, positioned to receive light scattered from said scattering measurement zone at a first angle $\theta_1$; and
   a second large angle light scattering photodetector, positioned to receive light scattered from said scattering measurement zone at a second angle $\theta_2$ wherein $\theta_2 > \theta_1$.

2. The analyzer of claim 1 wherein $\theta_2$ is between about 50° and 130°, and $\theta_1$ is between about 15° and 50°.

3. The analyzer of claim 2 wherein $\theta_2$ is about 90°±15°.

4. The analyzer of claim 3 wherein $\theta_1$ is about 30°±10°.

5. The analyzer of claim 2 wherein said sample flow is contained in a sample flow cell positioned at an oblique angle with respect to said light beam, wherein $\theta_2$ is about 73°±10° and $\theta_1$ is about 39°±10°.

6. The analyzer of claim 1 wherein said sample flow is contained in a sample flow cell positioned at a Brewster's angle with respect to said light beam.

7. The analyzer of claim 1 further comprising first and second collection optics for coupling scattered light into said first and second photodetectors, respectively.

8. The analyzer of claim 7 wherein neither said first nor said second collection optics comprises a polarizing filter.

9. The analyzer of claim 8 wherein neither said first nor said second collection optics comprises a wavelength filter.

10. The analyzer of claim 1 further comprising a forward angle light scattering photodetector positioned to receive light scattered from said scattering measurement zone at an angle $\theta_F$.

11. The analyzer of claim 10 further comprising a small angle light scattering photodetector positioned to receive light scattered from said scattering measurement zone at an angle $\theta_S$, where $\theta_F < \theta_S$.

12. The analyzer of claim 11 wherein $\theta_S$ is between about 2° and 10° and $\theta_F$ is between about 0° and about 3°.

13. The analyzer of claim 1 further comprising an absorption light source emitting an absorption light source beam positioned to illuminate a sample flow, the intersection of the absorption light source beam and the sample flow defining an absorption measurement zone, and a first absorption photodetector positioned to receive light transmitted through said absorption measurement zone.

14. The analyzer of claim 13 further comprising a second absorption photodetector positioned to receive light transmitted through said absorption measurement zone.

15. The analyzer of claim 1 further including a fluorescence photodetector positioned to receive fluorescent light from said scattering measurement zone.

16. A method for distinguishing polarization-preserving particles from depolarizing particles, comprising the steps of:
   flowing said particles through a p-polarized light beam;
   measuring the scattered light intensity $I(\theta_1)$ at a first large angle, $\theta_1$;
   measuring the scattered light intensity $I(\theta_2)$ at a second large angle, $\theta_2$, wherein $\theta_2 > \theta_1$; and comparing $I(\theta_1)$ to $I(\theta_2)$, thereby distinguishing polarization preserving particles from depolarizing particles.

17. An optical analyzer comprising:

a polarized light source positioned to produce a light beam which intersects a sample flow, the intersection defining a scattering measurement zone;

large angle light scattering photodetectors consisting essentially of:
 a first large angle light scattering photodetector, positioned to receive light scattered from said scattering measurement zone at a first angle $\theta_1$; and
 a second large angle light scattering photodetector, positioned to receive light scattered from said scattering measurement zone at a second angle $\theta_2$, wherein $\theta_2 > \theta_1$.

18. The analyzer of claim 17 wherein $\theta_2$ is between about 50° and 130°, and $\theta_1$ is between about 15° and 50°.

19. The analyzer of claim 17 wherein $\theta_2$ is about 90°±15°.

20. The analyzer of claim 17 wherein $\theta_1$ is about 30°±10°.

21. The analyzer of claim 17 wherein said sample flow is contained in a sample flow cell positioned at an oblique angle with respect to said light beam, wherein $\theta_2$ is about 73°±10° and $\theta_1$ is about 39°±10°.

22. The analyzer of claim 17 wherein said sample flow is contained in a sample flow cell positioned at a Brewster's angle with respect to said light beam.

23. The analyzer of claim 17 further comprising first and second collection optics for coupling scattered light into said first and second photodetectors, respectively.

24. The analyzer of claim 23 wherein neither said first nor said second collection optics comprises a polarizing filter.

25. The analyzer of claim 24 wherein neither said first nor said second collection optics comprises a wavelength filter.

26. The analyzer of claim 17 further comprising a forward angle light scattering photodetector positioned to receive light scattered from said scattering measurement zone at an angle $\theta_F$.

27. The analyzer of claim 26 further comprising a small angle light scattering photodetector positioned to receive light scattered from said scattering measurement zone at an angle $\theta_S$ where $\theta_F < \theta_S$.

28. The analyzer of claim 27 wherein said $\theta_S$ is between about 2° and 10° and $\theta_F$ is between about 0° and about 3°.

29. The analyzer of claim 17 further comprising an absorption light source emitting an absorption light source beam positioned to illuminate a sample flow, the intersection of said absorption light source beam and the sample flow defining an absorption measurement zone, and a first absorption photodetector positioned to receive light transmitted through said absorption measurement zone.

30. The analyzer of claim 29 further consisting essentially of a second absorption photodetector positioned to receive light transmitted through said absorption measurement zone.

31. The analyzer of claim 17 further including a fluorescence photodetector positioned to receive fluorescent light from said scattering measurement zone.

* * * * *

UNITED STATES PATENT AND TRADEMARK OFFICE
CERTIFICATE OF CORRECTION

PATENT NO.   : 6,067,157
DATED        : May 23, 2000
INVENTOR(S)  : Altendorf

It is certified that error appears in the above-identified patent and that said Letters Patent is hereby corrected as shown below:

Please delete FIG. 5 and replace with attached corrected FIG. 5

Column 3,
Line 24, please delete "having dual LALS, SALS, FALS, nad absorption detection" and replace with -- having detection capability for dual LALS, single SALS, single FALS, and dual absorption measurement --.

Column 10, claim 1,
Line 12, insert "large" between "first" and "angle".

Column 7,
Line 44, please delete the entire paragraph beginning with "FIG.13 shows..." and ending with "...second LALS detector–107-127°." The detection includes column 7, line 44 to line 67 and column 8, line 1 to line 4.

Signed and Sealed this

Twenty-ninth Day of January, 2002

Attest:

JAMES E. ROGAN
*Attesting Officer*   *Director of the United States Patent and Trademark Office*